United States Patent [19]

Orth et al.

[11] 4,357,277
[45] Nov. 2, 1982

[54] NOVEL PROCESS FOR THE PREPARATION OF N,N'-BISACYL HYDRAZIDES

[75] Inventors: Winfried Orth, Hassloch; Fritz W. Lange, Gauting; Werner Fickert, Mannheim-Seckenheim, all of Fed. Rep. of Germany

[73] Assignee: Rutgerswerke Aktiengesellschaft, Frankfurt am Main, Fed. Rep. of Germany

[21] Appl. No.: 224,128

[22] Filed: Jan. 12, 1981

[30] Foreign Application Priority Data

Feb. 23, 1980 [DE] Fed. Rep. of Germany ....... 3006806

[51] Int. Cl.³ ................. C07D 207/27; C07D 211/76; C07D 227/00; C07D 401/12
[52] U.S. Cl. ............................... 260/326.25; 546/188; 546/208
[58] Field of Search ...................... 260/326.25, 326.43; 546/208, 188; 564/134

[56] References Cited

U.S. PATENT DOCUMENTS 3,334,083  8/1967  Beyerman et al. ................. 564/134
3,867,424  2/1975  Fujimoto et al. .................. 564/134
4,069,336  1/1978  Lange et al. ....................... 260/326.43

OTHER PUBLICATIONS

Nevers et al., Chem. Abstracts, vol. 82, Abstract No. 73695h, (1975).

Primary Examiner—Alton D. Rollins
Attorney, Agent, or Firm—Hammond & Littell, Weissenberger and Muserlian

[57] ABSTRACT

An improved process for the preparation of acyl hydrazides of the formula

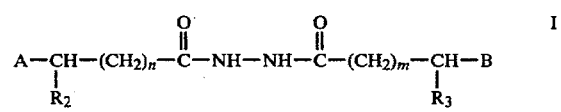

wherein A and B individually are a group of the formula

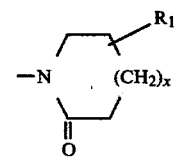

wherein $R_1$ is selected from the group consisting of hydrogen and alkyl of 1 to 4 carbon atoms, x is 0 or 1 and $R_2$ and $R_3$ are individually selected from the group consisting of hydrogen and alkyl of 1 to 4 carbon atoms and n and m are individually 0, 1, 2 or 3 by reacting a compound of the formula

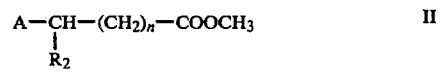

with a hydrazide of the formula

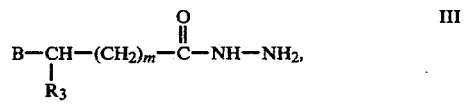

the improvement comprising effecting the reaction in the presence of at least one catalyst selected from the group consisting of amines, amine alkoxides and quaternary ammonium hydroxides.

9 Claims, No Drawings

NOVEL PROCESS FOR THE PREPARATION OF N,N'-BISACYL HYDRAZIDES

STATE OF THE ART

N,N'-bis-acyl hydrazides are prepared by reacting an ester with a corresponding acyl hydrazide as described in German DOS No. 2,440,633 or German patent application Ser. No. P 27 45 907. A hydrazide of formula III is reacted with an alkyl ester of the formula

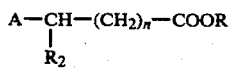

wherein R is alkyl of 1 to 4 carbon atoms, preferably methyl, but the yields of the process are uneconomically low, on the order of 5 to 55%.

OBJECTS OF THE INVENTION

It is an object of the invention to provide an improved, simple process for the preparation of acyl hydrazides of formula I in good yields and a high degree of purity.

This and other objects and advantages of the invention will become obvious from the following detailed description.

THE INVENTION

In the improved process of the invention for the preparation of acyl hydrazides of the formula

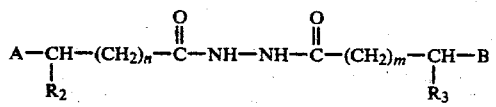

wherein A and B individually are a group of the formula

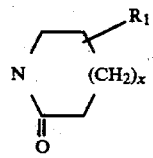

where $R_1$ is selected from the group consisting of hydrogen and alkyl of 1 to 4 carbon atoms x is 0 or 1 and $R_2$ and $R_3$ are individually selected from the group consisting of hydrogen and alkyl of 1 to 4 carbon atoms and n and m are individually 0, 1,2 or 3 by reacting a compound of the formula

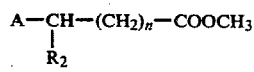

with a hydrazide of the formula

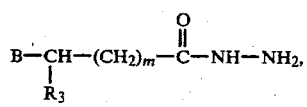

the improvement comprises effecting the reaction in the presence of at least one catalyst selected from the group consisting of amines, amine alkoxides and quaternary ammonium hydroxides. The said process results in substantially higher yields than the prior art process, on the average order of 70 to 80% of theory.

The amines may be primary, secondary or tertiary aliphatic, alicyclic or heterocyclic amines with at least one, preferably 1 to 3 amino groups in the molecule and mixtures thereof. The corresponding amine alkoxides may also be used as well as the corresponding quaternary ammonium hydroxides.

If the compounds of formula I are to be used as pharmaceuticals, the catalyst is preferably non-toxic, pharmaceutically acceptable organic amine such as dimethylaminoethanol or methyldiethanolamine which give excellent yields. The amount of amine is not critical and may vary between 0.01 to 50 mole percent, preferably 0.1 to 1.0, most preferably 0.05 to 2 mole percent, based on the compound of formula II or III.

Examples of suitable catalysts are amines such as dimethylaminoethanol, diethylaminoethanol, diethanolamine, diisopropylaminoethanolamine, triethanolamine, methyldiethanolamine, methylcyclohexylamine, 4-amino-pyridine, 1-benzyl-imidazole, 2-dimethylaminoethoxy pyridine, 4-dimethylaminopyridine, N,N-dimethyl-benzylamine, ephedrine, N-(2-hydroxyethyl)-morpholine, N-(2-hydroxyethyl)-piperazine, N-(2-hydroxyethyl)-piperidine, N-(2-hydroxyethyl)-pyrrolidine, 1-methylimidazole, 2-methyl-imidazole, N-methyl-morpholine, 1-methylpiperazine, N-methyl-piperidine, N-methyl-pyrrolidine, morpholine, piperazine, piperidine, pyrrolidine, 4-pyrrolidinopyridine, tetrahydro-isoquinoline, N,N,N',N''',N''-pentamethyldiethylenetriamine, N,N,N',N'-tetramethyl-ethylenediamine, benzyl triethylammonium hydroxide, benzyltrimethylammonium hydroxide, 4-cyclohexylaminopyridinium hydroxide, etc.

The compounds of formulae II and III are preferably reacted in substantially equimolar amounts of each or with a slight excess of about 0.1 to 0.4 moles of either one. The reaction may be effected in the absence of a solvent but is preferably effected in at least one inert organic solvent such as lower alkanols of 1 to 5 carbon atoms such as methanol or isopropanol or aromatic hydrocarbons such as toluene or xylene.

The reaction is most advantageously carried out at elevated temperatures such as 100° to 180° C., preferably 120° to 140° C. with the specific temperature depending on the specific catalyst used. Generally, when a quaternary ammonium hydroxide is used as the catalyst, the reaction temperature is 10° to 20° C. lower than with other catalysts under identical conditions. In some instances, it might be advisable to first cool the reaction mixture and the reaction may be effected at normal pressure, subatmospheric pressure or superatmospheric pressure and may be effected under an inert atmosphere such as nitrogen.

The compounds of formula I are known to possess valuable pharmacological properties and may be used in psychotheraphy, for example and the process is particularly useful for the preparation of N,N'-bis-(pyrrolidin-2-one-1-acetyl)-hydrazides.

The compounds of formula III can be prepared as described in German DOS 2,440,633 by the reaction of a compound of formula II with hydrazine and when the process is used to prepare symetrical bis-hydrazides, the compounds of formula III need not be isolated from the reaction mixture, but the additional amount of the compound of formula II is merely added thereto. In this latter embodiment, the amine may be added to the initial mixture of hydrazine and the compound of formula II but preferably, the amine is added to the mixture after the formation of the compound of formula III.

In the following examples there are described several preferred embodiments of the invention to illustrate the invention. However, it is to be understood that the invention is not intended to be limited to the specific embodiments.

EXAMPLE 1

N,N'-bis-(pyrrolidin-2-one-1-acetyl)-hydrazide

A mixture of 157 g (1 mole) of pyrrolidin-2-one-1-acetic acid anhydride, 157 g (1 mole) of methyl pyrrolidin-2-one-1-acetate, 9 g (0.1 mole) of dimethylaminoethanol and 300 ml of xylene was heated with vigorous stirring at 130°±1° C. for 24 hours while distilling off the methanol formed via a small column to maintain the desired temperature. The mixture was then cooled to 90° C. and 150 ml of isopropanol were added thereto. The mixture was then refluxed with stirring for one hour and was then cooled to room temperature. The mixture was vacuum filtered and the recovered product was rinsed 3 times with 150 ml of isopropanol and was dried in vacuo at 60° to 70° C. to obtain 215–219 g of N,N'-bis-(pyrrolidin-2-one-1-acetyl)-hydrazine melting at 202°–203° C. which was 77.6% of theory.

EXAMPLE 2

For comparative purposes, the procedure of Example 1 was repeated except dimethylaminoethanol was omitted and the yield of N,N'-bis-(pyrrolidin-2-one-1-acetyl)-hydrazide was only 50 to 54% of theory.

EXAMPLES 3 to 36

The procedure of Example 1 was repeated except dimethylaminoethanol was replaced with the amine catalysts of Table I and the yield of N,N'-bis-(pyrrolidin-2-one-1-acetyl)-hydrazide is indicated.

TABLE I

| Example No. | Amine Catalyst | Molar % of amine | % yield of theory |
|---|---|---|---|
| 3 | 4-Aminopyridine | 0.064 | 74.8 |
| 4 | 1-Benzylimidazole | 0.15 | 72.3 |
| 5 | Benzyl-triethylammonium hydroxide | 0.1 | 75.3 |
| 6 | Benzyl-trimethylammonium hydroxide | 0.1 | 76.0 |
| 7 | 4-Cyclohexylamino-pyridinium hydroxide | 0.07 | 73 |
| 8 | Diethanolamine | 0.12 | 73.1 |
| 9 | Diethylaminoethanol | 0.09 | 76.5 |
| 10 | Diethyl-(2-hydroxy-propyl)-amine | 0.12 | 72.4 |
| 11 | Diisopropylaminoethanol-amine | 0.12 | 73.2 |
| 12 | 2-Dimethylaminoethoxy-pyridine | 0.12 | 73.6 |
| 13 | 4-Dimethylaminopyridine | 0.065 | 75.5 |
| 14 | N,N—Dimethylbenzylamine | 0.14 | 74.8 |
| 15 | Ephedrine | 0.12 | 71.6 |
| 16 | N—2-Hydroxyethylmorpholine | 0.08 | 75.3 |
| 17 | N—2-Hydroxyethylpiperazine | 0.065 | 75.4 |
| 18 | N—2-Hydroxyethylpiperidine | 0.065 | 75.5 |
| 19 | N—2-Hydroxyethylpyrrolidine | 0.065 | 76.6 |
| 20 | Methyldiethanolamine | 0.1 | 80.5 |
| 21 | 1-Methylimidazole | 0.14 | 71 |
| 22 | 2-Methylimidazole | 0.14 | 74 |
| 23 | N—Methylmorpholine | 0.15 | 73.1 |
| 24 | 1-Methylpiperazine | 0.1 | 74 |
| 25 | N—methylpiperidine | 0.1 | 75.4 |
| 26 | N—Methylpyrrolidine | 0.1 | 75.8 |

TABLE I-continued

| Example No. | Amine Catalyst | Molar % of amine | % yield of theory |
|---|---|---|---|
| 27 | Methyl-cyclohexyl-amine | 0.1 | 73.2 |
| 28 | Morpholine | 0.1 | 72.1 |
| 29 | N,N,N',N'',N''—Pentamethyl-diethylentriamine | 0.07 | 76.3 |
| 30 | Piperazine | 0.1 | 73.4 |
| 31 | Piperidine | 0.1 | 74.3 |
| 32 | Pyrrolidine | 0.09 | 75.6 |
| 33 | 4-Pyrrolidinopyridine | 0.07 | 76.2 |
| 34 | N,N,N',N'—Tetramethyl-ethylendiamine | 0.1 | 75.5 |
| 35 | Tetrahydroisoquinoline | 0.12 | 72 |
| 36 | Triethanolamine | 0.092 | 75.5 |

EXAMPLE 37

N,N'-bis-(5-methyl-pyrrolidin-2-one-1-acetyl)-hydrazide

A solution of 8 g of N-methyl-pyrrolidine in 140 ml of xylene was added to a mixture of 171 g of 5-methyl-pyrrolidin-2-one-1-acetyl hydrazide and 171 g of methyl 5-methylpyrrolidin-2-one-1-acetate and the mixture was heated with stirring at 130° C. for 24 hours while distilling the methanol formed. After 5 hours, 60 ml of xylene were added dropwise over one to 2 hours to keep the crystallized product in suspension and the mixture was then cooled to 80° to 90° C. 60 ml of isopropanol were added to the mixture which was then stirred for 30 minutes and was then cooled to 20° C. The mixture was vacuum filtered and the damp recovered product was admixed with 150 ml of isopropanol. The mixture was stirred at room temperature for 5 hours and was vacuum filtered. The product was rinsed twice with 40 ml of isopropanol and was dried in vacuo at 70°–80° C. to obtain 232 g of N,N'-bis-(5-methyl-pyrrolidin-2-one-1-acetyl)-hydrazide melting at 181° C. which was 75% of theory.

EXAMPLE 38

N,N'-bis-[pyrrolidin-2-one-1-(3-propionyl)]-hydrazide

A mixture of 171 g of pyrrolidin-2-one-1-(3-propionyl)-hydrazide and 171 g of methyl pyrrolidin-2-one-1-(3-propionate) and a solution of 8 g of N-methyl-pyrrolidine in 140 ml of xylene was heated at 130° C. with stirring for 24 hours and was then cooled. 400 ml of isopropanol were added to the mixture which was refluxed for 30 minutes with stirring and was then cooled to room temperature. The mixture was vacuum filtered and the recovered product was rinsed with isopropanol and dried at 50° C. to obtain 167 g of N,N'-bis-[pyrrolidin-2-one-1-(3-propionyl)]-hydrazide melting at 228° C. (decomposition) for a yield of 53.8% of theory.

EXAMPLE 39

N-(pyrrolidin-2-one-1-acetyl-N'-(5-methyl-pyrrolidin-2-one-1-acetyl)-hydrazide

A mixture of 171 g of 5-methyl-pyrrolidin-2-one-1-acetyl hydrazide and 157 g of methyl pyrrolidin-2-one-1-acetate and a solution of 8 g of dimethylaminoethanol in xylene was heated with stirring at 130° C. for 24 hours and was then cooled. 400 ml of isopropanol were added to the mixture which was then refluxed for 30 minutes with stirring and was then cooled. The mixture was vacuum filtered and the recovered product was rinsed with isopropanol and dried at 50° C. to obtain 157 g of N-(pyrrolidin-2-one-1-acetyl)-N'-(5-methyl-pyrrolidin-2-one-1-acetyl)-hydrazide melting at 159°–160° C. for a yield of 53% of theory.

Various modifications of the process of the invention may be made without departing from the spirit or scope thereof and it is to be understood that the invention is intended to be limited only as defined in the appended claims.

We claim:

1. In a process for the preparation of acyl hydrazides of the formula

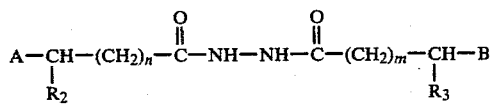   I wherein A and B individually are a group of the formula

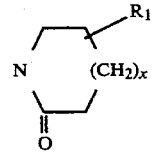

wherein $R_1$ is selected from the group consisting of hydrogen and alkyl of 1 to 4 carbon atoms, x is 0 or 1 and $R_2$ and $R_3$ are individually selected from the group consisting of hydrogen and alkyl of 1 to 4 carbon atoms and n and m are individually 0, 1, 2 or 3 by reacting a compound of the formula

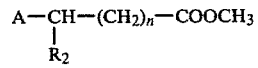   II with a hydrazide of the formula

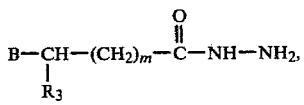   III the improvement comprising effecting the reaction in the presence of at least one catalyst selected from the group consisting of primary, secondary or tertiary aliphatic, alicyclic and heterocyclic amines having 1 to 3 amino groups and amine alkoxides and quaternary ammonium hydroxides derived from said amines.

2. The process of claim 1 wherein the amount of amine is 0.01 to 1.0 mole-percent based on the amount of the compound of formula II or III.

3. The process of claim 2 wherein the amount is 0.05 to 0.2 mole-percent.

4. The process of claim 1 wherein the reaction is effected at 100° to 180° C.

5. The process of claim 1 wherein the reaction is effected at 120° to 140° C.

6. The process of claim 1 wherein the catalyst is dimethylaminoethanol.

7. The process of claim 1 wherein the catalyst is methyldiethanolamine.

8. The process of claim 1 wherein A and B are pyrrolidin-2-one, $R_2$ and $R_3$ are hydrogen and n and m are 0.

9. The process of claim 1 wherein the compound of formula III is formed by reacting a compound of formula II with hydrazine and the latter is reacted without isolation with another mole of the compound of formula II to form a symetrical bishydrazide.

* * * * *

UNITED STATES PATENT AND TRADEMARK OFFICE
CERTIFICATE OF CORRECTION

PATENT NO. : 4,357,277
DATED : November 2, 1982
INVENTOR(S) : WINFRIED ORTH ET AL.

It is certified that error appears in the above-identified patent and that said Letters Patent is hereby corrected as shown below:

Column 3, line 14: "acetic acid anhydride" should read
-- acetyl hydrazide --.

Column 3, line 15: "dimethylaminoe-" should read
-- dimethylamino- --.

Column 3, line 16: "thanol" should read -- ethanol --.

Column 4, Line 56: " ... acetyl-N'- ..." should read
-- ... acetyl)-N'- ... --.

Signed and Sealed this

Twenty-second Day of March 1983

[SEAL]

Attest:

GERALD J. MOSSINGHOFF

Attesting Officer    Commissioner of Patents and Trademarks